United States Patent [19]
Kolstedt

[11] 4,335,726
[45] Jun. 22, 1982

[54] THERAPEUTIC DEVICE WITH TEMPERATURE AND PRESSURE CONTROL

[75] Inventor: Mark W. Kolstedt, Cary, Ill.

[73] Assignee: The Kendall Company, Boston, Mass.

[21] Appl. No.: 167,493

[22] Filed: Jul. 11, 1980

[51] Int. Cl.³ ........ A61F 7/00
[52] U.S. Cl. ........ 128/400; 128/402
[58] Field of Search ........ 128/400, 402, 399, 64, 128/327, 254; 165/46

[56] References Cited

U.S. PATENT DOCUMENTS

| | | | |
|---|---|---|---|
| 484,182 | 10/1882 | Dewey . | |
| 2,190,384 | 2/1940 | Newman | 128/400 |
| 3,074,410 | 1/1963 | Foster | 128/400 |
| 3,088,288 | 5/1963 | Elfving . | |
| 3,153,414 | 10/1964 | Beall et al. | 128/327 X |
| 3,186,404 | 6/1965 | Gardner | 128/87 |
| 3,238,944 | 3/1966 | Hirschhorn | 128/400 |
| 3,262,492 | 7/1966 | Meenan . | |
| 3,738,372 | 6/1973 | Shioshvili | 128/400 |
| 3,865,116 | 2/1975 | Brooks | 128/400 |
| 3,871,381 | 3/1975 | Roslonski | 128/400 |
| 3,967,627 | 7/1976 | Brown | 128/400 |
| 4,159,541 | 4/1979 | Gammons et al. | 128/400 |
| 4,259,961 | 4/1981 | Hood | 128/400 |

FOREIGN PATENT DOCUMENTS 1262837 4/1961 France .

OTHER PUBLICATIONS

Cryopac-Brochure pub. by Cryomed Devices, Inc., Princeton, New Jersey, ©1974.
Thermoelectric Coolers-EDN, May 20, 1980.

*Primary Examiner*—F. Barry Shay
*Attorney, Agent, or Firm*—Powell L. Sprunger

[57] ABSTRACT

A therapeutic device comprising, a sleeve for covering a portion of a patient's body and having flexible walls defining an inner space to receive liquid, a conduit system connected to the space, and a device for circulating a liquid through the conduit system and the sleeve space. The therapeutic device has a device for changing the temperature of the circulating liquid in the conduit system, and a device for pressurizing the liquid in the sleeve space.

9 Claims, 6 Drawing Figures

67 62 44 66 58 COLD 60 64 HOT 85 20 82 84 90 HOT COLD 86 88 54 56 38 40 42 80 38 24 50 P 26 28 22 30 52 36 34 32 31 134 130 132 126 128 144 27 138 142 136 140

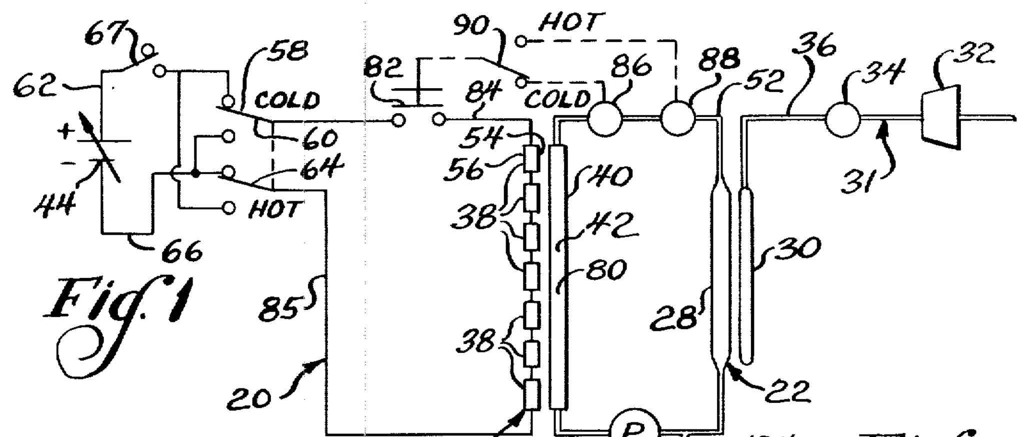
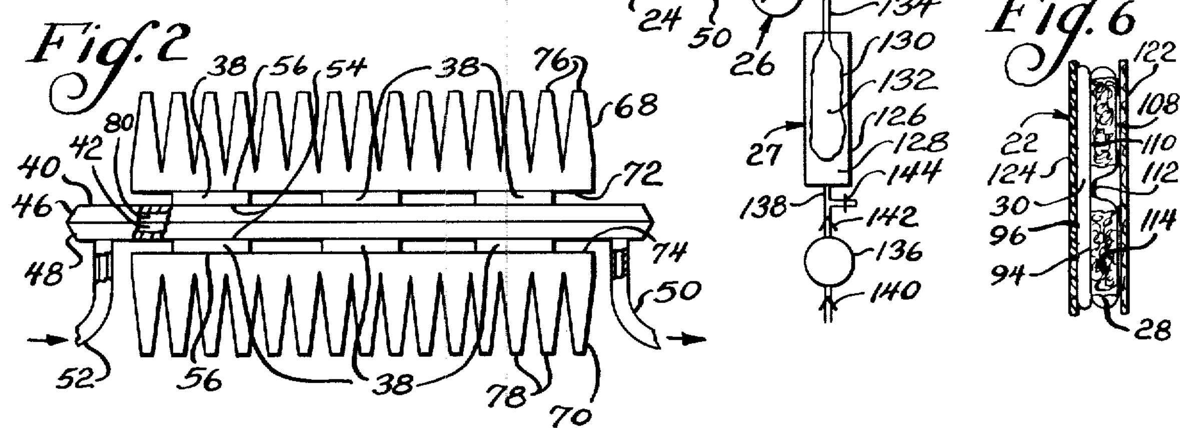
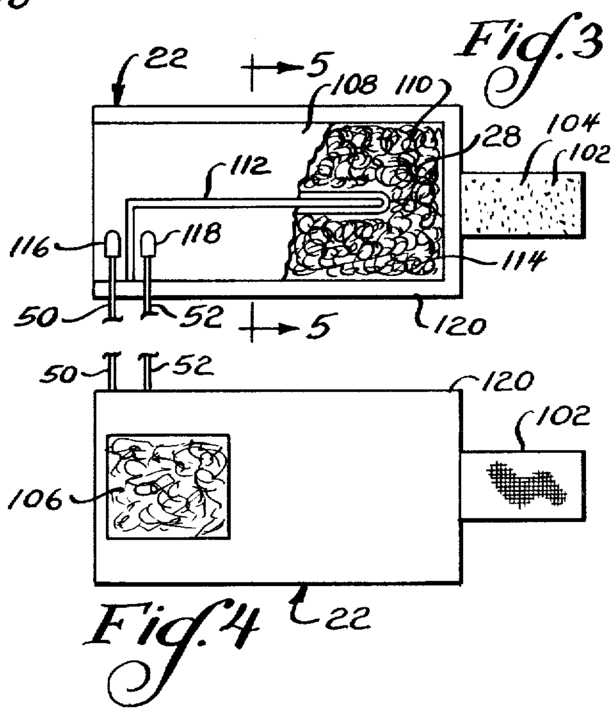
Fig. 5
22 28 120 114 112 108 110

THERAPEUTIC DEVICE WITH TEMPERATURE AND PRESSURE CONTROL

BACKGROUND OF THE INVENTION

The present invention relates to therapeutic devices for patients.

Cryotherapy may be defined as the treatment of a patient with cold. In many instances it is desirable to cool and apply pressure to the tissue of the patient. For example, sports trainers often wish to apply cold and pressure to the extremities, hands, feet, or joints of an athlete after a sprain or strain sustained during playing. Similarly, physicians in hospitals, such as in emergency rooms, often desire to apply cold and pressure to a patient in order to accelerate healing by reducing edema and hematoma. It is also believed that the application of cold and pressure may be useful for spinal injuries. Not only does cold and pressure serve for the treatment of tissue injuries, it also acts as an anesthetic to reduce pain.

In the past, the necessary coldness has been most commonly obtained through the use of ice. It is apparent that such a procedure is cumbersome and inconvenient, and the desired coldness may not be obtained. In certain instances, it is desirable to apply cold and pressure for protracted periods of time which is not feasible without frequent changes of ice. In some instances, it is desirable to apply heat after cryotherapy has been completed which of course cannot be accomplished with ice.

SUMMARY OF THE INVENTION

A principal feature of the present invention is the provision of a therapeutic device for use in cryotherapy.

The device of the present invention comprises, a sleeve for covering a portion of a patient's body and having flexible walls defining an inner space to receive liquid, a conduit system connected to the space, means for circulating a liquid through the conduit system and the sleeve space, and means for changing the temperature of the circulating liquid in the conduit system.

A feature of the present invention is the provision of means for pressurizing the liquid in the sleeve space.

Thus, another feature of the present invention is that the pressurizing means may be utilized to enhance the pressure exerted by the sleeve against the patient's body.

Still another feature of the invention is that the pressurizing means may be utilized to pressurize the liquid in the sleeve space a desired amount by the user.

Further features will become more fully apparent in the following description of the embodiments of this invention and from the appended claims.

DESCRIPTION OF THE DRAWINGS

In the drawings:

FIG. 1 is a schematic view of a therapeutic device of the present invention;

FIG. 2 is a fragmentary side elevational view, partly broken away, of a cooling and heating device for the device of FIG. 1;

FIG. 3 is a fragmentary front plan view, partly broken away, of a sleeve for the device of FIG. 1;

FIG. 4 is a fragmentary back plan view of the sleeve of FIG. 3;

FIG. 5 is a sectional view taken substantially as indicated along the line 5—5 of FIG. 3; and FIG. 6 is a sectional view of another embodiment of a sleeve for the device of FIG. 1.

DESCRIPTION OF THE PREFERRED EMBODIMENTS

Referring now to FIG. 1, there is shown a therapeutic device generally designated 20 comprising a sleeve 22 for covering a portion of a patient's body, such as the extremities, a cooling and heating device 24, a device such as a pump 26 for circulating liquid through the sleeve 22 and device 24, and a device 27 for pressurizing the liquid in the system. As will be further discussed below, the sleeve 22 has flexible walls defining an inner space 28 to receive the circulating liquid, and may have an inflatable external chamber 30 to apply pressure in the sleeve 22 against the space 28 which is retained adjacent the patient's body. The device 20 may have an inflation device 31 comprising an air compressor 32 and a pressure regulator 34 in order to inflate the chamber 30 through a conduit 36.

The cooling and heating device 24 comprises a plurality of thermoelectric devices or thermoelectric cooling modules 38, a metallic container 40 having a chamber 42 to retain a liquid 80 such as water or antifreeze, and a variable direct current power supply 44. With reference to FIGS. 1 and 2, the container 40 comprises a pair of metallic shells 46 and 48 which have cavities such that the shells 46 and 48 define the chamber 42 when the shells 46 and 48 are placed together. In a suitable form, the shells 46 and 48 may be constructed from copper in order to facilitate heat transfer through the shells 46 and 48. The device 20 has an outlet conduit 50 communicating with the chamber 42 and one side of the sleeve space 28, with the pump 26 being connected to the conduit 50, as shown. The device 20 also has an inlet conduit 52 communicating between the chamber 42 and the other side of the sleeve space 28. During operation, the pump 26 circulates the cooling and heating liquid 80 through the conduit 50, the sleeve space 28, the conduit 52, and the container chamber 42, such that the described arrangement circulates the liquid 80 between the container 40, where the liquid is cooled or heated, and the sleeve 22 through use of the pump 26.

The thermoelectric devices 38 operate in the following manner. When direct current is passed in one direction through the thermoelectric devices 38, one side or face 43 of the thermoelectric devices 38 is cooled, while the other side or face 56 of the thermoelectric devices 38 is heated. When the direction of the direct current through the thermoelectric devices 38 is reversed, the one face 54 of the thermoelectric devices 38 is heated, while the other face 56 of the thermoelectric devices 38 is cooled. The device 20 has a double pole, double throw switch 58 in order to control the direction of current through the thermoelectric devices 38, with the switch 58 being connected to the thermoelectric devices 38, which are connected in series, by a pair of leads 84 and 85. When the switch 58 is connected to the "cold" setting, as shown, with the contact 60 and lead 84 being connected to the lead 62, and with the contact 64 and lead 85 being connected to the lead 66, the direction of the current from the power supply 44 through the thermoelectric devices 38 is such that the one face 54 of the devices 38 is cooled, while the other face 56 of the devices 38 is heated. When the switch 58 is moved to the "hot" setting, with the contact 60 and lead 84 being connected to the lead 66, and with the contact 64 and lead 85 being connected to the lead 62, the direction of the current from the power supply 44 through the thermoelectric devices 38 is reversed, such that the one face 54 of the thermoelectric devices 38 is heated, while the other face 56 of the thermoelectric devices 38 is cooled. The lead 62 may have an on/off switch 67 in order to control application of power to the thermoelectric devices 38.

With reference to FIG. 2, the thermoelectric devices 38 are placed on opposed sides of the container 40, with the one face 54 of the thermoelectric devices 38 facing toward and in contact with the walls of the container 40, and with the other face 56 of the thermoelectric devices 38 facing away from the container 40. In the illustrated configuration, three thermoelectric devices 38 are placed on one side of the container 40, and three thermoelectric devices 38 are placed on the other side of the container 40. As shown, the device 20 has a pair of heat sinks 68 and 70 having generally planar surfaces 72 and 74, respectively, and a plurality of fins 76 and 78, respectively. The surfaces 72 and 74 of the heat sinks 68 and 70 are in contact with the other face 56 of the thermoelectric devices 38. As previously discussed in connection with FIGS. 1 and 2, when the switch 58 is connected to the "cold" setting, the one face 54 of the thermoelectric devices 38 is cooled, and the other face 56 of the thermoelectric devices 38 is heated. In this switch configuration, the heat sinks 68 and 70 are utilized to dissipate heat from the other face 56 of the thermoelectric devices 38, while the one face 54 of the thermoelectric devices 38 cools the liquid 80 in the chamber 42 through the metallic shells 46 and 48.

Thus, when the switch 58 is placed in the "cold" setting, the liquid 80 is cooled in the container chamber 42, and the pump 26 circulates the cooled liquid 80 through the conduit 50 to the space 28 in the sleeve 22, with the pump 26 also recirculating the liquid 80 from the sleeve space 28 through the conduit 52 to the container chamber 42 for additional cooling. Of course, during use of the device 20, the sleeve space 28 is placed toward the patient in order to cool the patient's body by the cold liquid in the space 28. Alternatively, when the switch 58 is placed in the "hot" setting, the liquid 80 in the container chamber 42 is heated, and the pump 26 circulates the heated liquid 80 through the conduit 50 into the sleeve space 28, with the pump 26 also recirculating the liquid 80 from the space 28 through the conduit 52 to the container chamber 42 for additional heating. Thus, in this configuration of the switch 58, the sleeve space 28 may be utilized to apply heat to the patient's body. Accordingly, the device 20 may apply cold or heat to the patient for treatment in accordance with the setting of the switch 58.

As shown in FIG. 1, the device 20 has a switch or relay 82 operatively associated with the lead 84. The device 20 may have a pair of thermostats 86 and 88, such as temperature sensors, which measure the temperature of the liquid 80 in the circulating system. The device 20 may have a switch 90 to control the operative connection of the thermostats 86 and 88 to the switch or relay 82. When the switch 90 is placed in the "cold" setting, the thermostat 86 is operatively connected to the switch or relay 82 such that the switch 82 is closed or the relay 82 is placed in the closed setting when the thermostat 86 determines that the cooling liquid 80 is not sufficiently cold in order to provide current to the thermoelectric devices 38 and cause cooling; of course, the switch 58 is also placed in the "cold" setting at this time. On the other hand, the switch 82 is opened or the relay 82 is placed in the open setting when the thermostat 86 determines that the liquid 80 is at or below the desired temperature, in order to remove current from the thermoelectric devices 38 and stop cooling. Alternatively, when the switch 90 is placed in the "hot" setting, the switch 82 is closed or the relay 82 is placed in the closed setting when the thermostat 88 determines that the liquid is not sufficiently hot in order to provide current to the thermoelectric devices 38 and cause heating; of course, the switch 58 is also placed in the "hot" setting at this time. On the other hand, the switch 82 is opened or the relay 82 is placed in the open setting when the thermostat 88 determines that the temperature is at or above the desired temperature of the circulating liquid 80 in order to remove current from the thermoelectric devices 38 and stop heating. Thus, the temperature of the circulating liquid 80 may be controlled whether the liquid 80 is being cooled or heated. In an alternative form, the switch or relay 82 may be closed, and the voltage of the power supply 44 may be varied in order to change the current through the thermoelectric devices 38 and raise or lower the temperature, as desired.

With reference to FIG. 1, the pressurizing device 27 has a rigid cylinder or receptacle 126 defining a closed chamber 128. The pressurizing device 27 also has a container or bag 130 with flexible walls defining a cavity 132, with the container 130 being received in the receptacle chamber 128, and with the container cavity 132 being connected to a conduit 134 which communicates with the conduit 50.

The pressurizing device also has a pump 136 comprising a hollow elastic bulb, with the pump 136 being connected by a conduit 138 with the chamber 128 outside the container 130. The pressurizing device 27 also has a first one-way valve 140 which permits passage of air from the atmosphere into the inside of the pump 136, and which prevents passage of air from the inside of the pump 136 to the atmosphere. The pressurizing device has a second one-way valve 142 in the conduit 138 which permits passage of air from the inside of the pump 136 to the receptacle chamber 128 outside the container 130, and which prevents the passage of air from the receptacle chamber 128 to the pump 136. The pressurizing device 27 also has a relief valve 144 connected to the conduit 138, such that the valve 144 may be opened to connect the receptacle chamber 128 to the atmosphere through the valve 144, or the valve 144 may be closed in order to close the receptacle chamber 128 to the atmosphere.

In operation, the relief valve 144 is first opened in order to establish atmospheric pressure in the receptacle chamber 128, with liquid being retained in the container cavity 132 at this time. Next, the sleeve 22 is placed about the extremity of a patient in order to locate the space 28 adjacent the skin of the patient. After placement of the sleeve 22, the pump 136 is squeezed by the hands of the user in order to force air through the valve 142 and conduit 138 into the receptacle chamber 128, and the pump 136 is then released to permit passage of air from the atmosphere through the valve 140 into the pump 136. The pump may be repetitively squeezed in order to repetitively pump air from the bulb or pump 136 into the receptacle chamber 128. In this manner, the receptacle chamber 128 outside the container 130 is pressurized by air a desired amount through use of the pump 136. In turn, the flexible walls of the container 130 are squeezed by the pressurized air in order to force liquid from the container cavity 132 through the conduit 134 into the conduit system and the sleeve space 28 which expands due to the increasing liquid in the space 28. Thus, the pressurizing device 27 is utilized to inject an additional quantity of liquid into the sleeve space 28 in order to apply pressure by the cooled or heated space 28 against the patient's extremity.

A sleeve 22 for the device 20 is illustrated in FIGS. 3-5. The sleeve 22 has a front wall 108 of flexible plastic material, and a back wall 110 of flexible plastic material. The front and back walls 108 and 110 are joined at their peripheries, such as by heat sealing, and along an intermediate line 112 to define the space 28 intermediate the front and back walls 108 and 110. The sleeve 22 has a sheet 114 of open cell foam which is cut to the size of the space 28 and which is placed in the space 28 between the front and back walls 108 and 110. The sleeve 22 has a pair of connectors 116 and 118 connected to the front wall 108 on opposed sides of the sealing line 112, with the connectors 116 and 118 communicating with the space 28 in the sleeve 22. As shown, the outlet conduit 50 is connected to the connector 116, and the inlet conduit 52 is connected to the connector 118, such that the conduits 50 and 52 communicate with the opposed ends of the serpentine space 28 in the sleeve 22.

The sleeve 22 has a rear sheet 120 of insulation material, such as closed cell foam, covering the back wall 110. The sleeve 22 has a strap 102 extending from one end of the sheet 120, with a strip 104 of hook fastening material being secured on the front face of the strap 102. The sleeve 22 also has a sheet 106 of loop fastening material secured to an outer face of the sheet 120 adjacent the other end of the sheet 120.

In use, the front wall 108 of the sleeve 22 is placed against the extremity of a patient, and the sleeve is wrapped around the extremity. Next, the hook fastening strip 104 on the strap 102 is secured to the sheet 106 of loop fastening material in order to secure the sleeve 22 in place on the extremity and apply pressure by the sheet 120 against the walls 108 and 110 defining the space 28. Next, the pressurizing device 27 is operated by the pump 136 to inject an additional quantity of liquid from the container cavity 132 into the sleeve space 28 resulting in additional pressure by the space 28 in the secured sleeve 22. The cold or hot liquid 80 is then circulated through the conduits 50 and 52 and through the space 28 between the walls 108 and 110 in order to apply cold or heat to the patient's extremity through the front wall 108 while the sheet 120 applies pressure by the sleeve 22 against the patient's extremity. When secured to the patient, the sheet 120 serves to insulate the circulating cold or hot liquid 80 in order to limit passage of heat to or from the liquid 80 in the space 28. Also, the resilient sheet 114 of open cell foam material permits passage of liquid, but maintains the walls 108 and 110 in a spaced apart configuration at a plurality of locations, such that the applied pressure does not impede flow of liquid through the space 28. In addition, the sheet 114 of open cell foam causes circulation and mixture of the liquid in the space 28 in order to provide a more uniform distribution of temperature in the space 28. After cooling or heating has been completed, the valve 142 may be opened to permit atmospheric pressure in the chamber 128 and retraction of liquid into the container cavity 132.

Another embodiment of the sleeve 22 for the device 20 is illustrated in FIG. 6, in which like reference numerals designate like parts. In this embodiment, the sleeve 22 has a front and back wall 108 and 110 which are joined together to define space 28 and which receive a sheet 114 of open cell foam intermediate the walls 108 and 110 in a manner as previously described in connection with the sleeve 22 of FIGS. 3-5. Also, the sleeve 22 may have a front wall 94 and a back wall 96 of flexible plastic material joined together at their peripheries in order to define an inflatable chamber 30 intermediate the walls 94 and 96 which is connected by conduit 36 to the inflation device 31. The sleeve 22 may have a front sheet 122 of flexible conformable material, such as a nonwoven material, with the sheet 122 covering the front wall 108. In addition, the sleeve 22 may have a back sheet 124 of flexible inelastic material, such as a suitable textile material.

In use, the sleeve 22 of FIG. 6 is wrapped around the patient's extremity and may be secured in place using hook and loop fastening strips in a manner as previously described in connection with the sleeve of FIGS. 3-5. Next, the chamber 30 may be inflated by the inflation device 31 in a manner as previously described in order to apply pressure by the sleeve 22 against the patient's extremity, with the outer sheet 124 limiting expansion of the chamber 30 to enhance the pressures applied by the sleeve 22. The pressurizing device 27 may then be operated to inject additional liquid into the conduit system and sleeve space 28 in order to apply additional pressure by the sleeve against the patient's extremity. The hot or cold liquid 80 may then be passed into the space 28 in order to apply heat or cold through the sheet 122 to the patient's extremity, while the sheet 114 of open cell foam maintains the space 28 in an open configuration. During use of the sleeve 22, the sheet 122 provides a comfortable surface of the sleeve 22 for contacting the patient's skin.

The foregoing detailed description is given for clearness of understanding only, and no unnecessary limitations should be understood therefrom, as modifications will be obvious to those skilled in the art.

I claim:

1. A therapeutic device, comprising:

a sleeve for covering a portion of a patient's body and having flexible walls defining an inner space to receive liquid;

means for changing the temperature of said liquid;

a conduit system connecting the sleeve space and the changing means in a pair of paths;

pump means for circulating the liquid between the sleeve space and changing means through the conduit system; and means for pressurizing the liquid in said sleeve space comprising, a receptacle having a chamber, a container in the receptacle chamber and having flexible walls defining a cavity containing liquid and communicating with the conduit system and sleeve space, and means for pressurizing the receptacle chamber outside said container to inject a desired amount of liquid from the container cavity into the conduit system and sleeve space.

2. The device of claim 1 wherein the temperature changing means comprises means for cooling the circulating liquid.

3. The device of claim 1 wherein the temperature changing means comprises means for heating the circulating liquid.

4. The device of claim 1 wherein said sleeve includes a sheet of flexible material outside said walls.

5. The device of claim 1 wherein said sleeve includes a pair of flexible walls outside said space defining a chamber, and means for inflating said chamber.

6. The device of claim 1 including a sheet of open cell foam in said space.

7. The device of claim 1 wherein the receptacle pressurizing means comprises means for pumping air into the receptacle chamber outside said container.

8. The device of claim 7 including means for selectively connecting the receptacle chamber outside said container to the atmosphere.

9. The device of claim 7 wherein the pumping means comprises a hollow elastic pump member, first one-way valve means permitting passage of air from the atmosphere into the pump member and preventing passage of air from the pump member to the atmosphere, and second one-way valve means permitting passage of air from the pump member into the receptacle chamber and preventing passage of air from the receptacle chamber to the pump member.

* * * * *